(12) United States Patent
Cheng et al.

(10) Patent No.: US 9,458,243 B2
(45) Date of Patent: Oct. 4, 2016

(54) SECONDARY ANTIBODY DETECTED EPITOPE AND PREPARATION OF SAME

(71) Applicant: KAOHSIUNG MEDICAL UNIVERSITY, Kaohsiung (TW)

(72) Inventors: Tian-Lu Cheng, Kaohsiung (TW); Steve Roffler, Taipei (TW); Wen-Wei Lin, Hsinchu (TW); I-Ju Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 27 days.

(21) Appl. No.: 14/534,174

(22) Filed: Nov. 6, 2014

(65) Prior Publication Data
US 2015/0315265 A1    Nov. 5, 2015

(30) Foreign Application Priority Data
May 1, 2014    (TW) .............................. 103115717 A

(51) Int. Cl.
*C07K 16/42*    (2006.01)
*C07K 16/00*    (2006.01)

(52) U.S. Cl.
CPC ........... *C07K 16/4283* (2013.01); *C07K 16/00* (2013.01); *C07K 2317/52* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,427,594 B1 * | 9/2008 | Yu ........................ | C07K 14/515 514/1.1 |
| 2005/0064395 A1 * | 3/2005 | Israel ..................... | B82Y 15/00 435/5 |
| 2012/0009621 A1 * | 1/2012 | Yamasaki .............. | C07K 16/00 435/69.6 |

\* cited by examiner

*Primary Examiner* — Jacob Cheu
(74) *Attorney, Agent, or Firm* — Hannah M. Tien

(57) ABSTRACT

A method of preparing an epitope for a secondary antibody detected protein tag, comprising: constructing a expressing vector, comprising a nucleotide sequence for encoding the secondary antibody detected protein tag comprising at least one epitope selected from at least one primary antibody which is detected by corresponding secondary antibody; expressing the vector in a host cell; and obtaining the secondary antibody detected protein tag which is expressed in the host cell. Further, a method for constructing a protein molecular weight marker ladder, comprising constructing a plurality of recombinant protein tags with different molecular weights, wherein each the recombinant protein tag comprises at least one epitope of primary antibody. Besides, a secondary antibody detected protein tag comprises at least two peptide sequences of epitopes selected from primary antibodies of at least two different species.

4 Claims, 9 Drawing Sheets

SEQUENCE LISTING

```
<160> NUMBER OF SEQ ID NOS: 13

<210> SEQ ID NO 1
<211> LENGTH: 53
<212> TYPE: PRT
<213> ORGANISM: Artificial Sequence
<220> FEATURE:
<223> OTHER INFORMATION: mouse antibody 1
<220> FEATURE:
<221> NAME/KEY: PEPTIDE
<222> LOCATION: (1)..(53)

<400> SEQUENCE: 1

Gln Pro Ile Met Asn Thr Asn Gly Ser Tyr Phe Val Tyr Ser Lys Leu
1               5                   10                  15

Asn Val Gln Lys Ser Asn Trp Glu Ala Gly Asn Thr Phe Thr Cys Ser
            20                  25                  30
```

```
Val Leu His Glu Gly Leu His Asn His His Thr Glu Lys Ser Leu Ser
        35                  40                  45

His Ser Pro Gly Leu
    50

<210> SEQ ID NO 2
<211> LENGTH: 54
<212> TYPE: PRT
<213> ORGANISM: Artificial Sequence
<220> FEATURE:
<223> OTHER INFORMATION: mouse antibody 2
<220> FEATURE:
<221> NAME/KEY: PEPTIDE
<222> LOCATION: (1)..(53)

<400> SEQUENCE: 2

Glu Phe Lys Cys Arg Val Asn Ser Ala Ala Phe Pro Ala Pro Ile Glu
1               5                   10                  15

Lys Thr Ile Ser Lys Thr Lys Gly Arg Pro Lys Ala Pro Gln Val Tyr
            20                  25                  30

Thr Ile Pro Pro Pro Lys Glu Gln Met Ala Lys Asp Lys Val Ser Leu
        35                  40                  45

Thr Cys Met Ile Thr Asp
    50

<210> SEQ ID NO 3
<211> LENGTH: 53
<212> TYPE: PRT
<213> ORGANISM: Artificial Sequence
<220> FEATURE:
<223> OTHER INFORMATION: mouse antibody 3
<220> FEATURE:
<221> NAME/KEY: PEPTIDE
<222> LOCATION: (1)..(53)

<400> SEQUENCE: 3

Gln Pro Ile Met Asn Thr Asn Gly Ser Tyr Phe Val Tyr Ser Lys Leu
1               5                   10                  15

Asn Val Gln Lys Ser Asn Trp Glu Ala Gly Asn Thr Phe Thr Cys Ser
            20                  25                  30

Val Leu His Glu Gly Leu His Asn His His Thr Glu Lys Ser Leu Ser
        35                  40                  45

His Ser Pro Gly Leu
    50

<210> SEQ ID NO 4
<211> LENGTH: 63
<212> TYPE: PRT
<213> ORGANISM: Artificial Sequence
<220> FEATURE:
<223> OTHER INFORMATION: rabbit antibody 1
<220> FEATURE:
<221> NAME/KEY: PEPTIDE
<222> LOCATION: (1)..(63)

<400> SEQUENCE: 4

Pro Lys Asp Thr Leu Met Ile Ser Arg Thr Pro Glu Val Thr Cys Val
1               5                   10                  15

Val Val Asp Val Ser Gln Asp Asp Pro Glu Val Gln Phe Thr Trp Tyr
            20                  25                  30
```

```
Ile Asn Asn Glu Gln Val Arg Thr Ala Arg Pro Pro Leu Arg Glu Gln
            35                  40                  45

Gln Phe Asn Ser Thr Ile Arg Val Val Ser Thr Leu Pro Ile Thr
         50                  55                  60
```

<210> SEQ ID NO 5
<211> LENGTH: 66
<212> TYPE: PRT
<213> ORGANISM: Artificial Sequence
<220> FEATURE:
<223> OTHER INFORMATION: rabbit antibody 2
<220> FEATURE:
<221> NAME/KEY: PEPTIDE
<222> LOCATION: (1)..(66)

<400> SEQUENCE: 5

```
Gly Lys Glu Phe Lys Cys Lys Val His Asn Lys Ala Leu Pro Ala Pro
1               5                   10                  15

Ile Glu Lys Thr Ile Ser Lys Ala Arg Gly Gln Pro Leu Glu Pro Lys
            20                  25                  30

Val Tyr Thr Met Gly Pro Pro Arg Glu Glu Leu Ser Ser Arg Ser Val
            35                  40                  45

Ser Leu Thr Cys Met Ile Asn Gly Phe Tyr Pro Ser Asp Ile Ser Val
         50                  55                  60

Glu Trp
65
```

<210> SEQ ID NO 6
<211> LENGTH: 65
<212> TYPE: PRT
<213> ORGANISM: Artificial Sequence
<220> FEATURE:
<223> OTHER INFORMATION: rabbit antibody 3
<220> FEATURE:
<221> NAME/KEY: PEPTIDE
<222> LOCATION: (1)..(65)

<400> SEQUENCE: 6

```
Lys Asn Gly Lys Ala Glu Asp Asn Tyr Lys Thr Thr Pro Ala Val Leu
1               5                   10                  15

Asp Ser Asp Gly Ser Tyr Phe Leu Tyr Asn Lys Leu Ser Val Pro Thr
            20                  25                  30

Ser Glu Trp Gln Arg Gly Asp Val Phe Thr Cys Ser Val Met His Glu
            35                  40                  45

Ala Leu His Asn His Tyr Thr Gln Lys Ser Ile Ser Arg Ser Pro Gly
         50                  55                  60

Lys
65
```

<210> SEQ ID NO 7
<211> LENGTH: 6
<212> TYPE: PRT
<213> ORGANISM: Artificial Sequence
<220> FEATURE:
<223> OTHER INFORMATION: His tag
<220> FEATURE:
<221> NAME/KEY: PEPTIDE
<222> LOCATION: (1)..(6)

<400> SEQUENCE: 7

```
His His His His His His
1               5
```

```
<210> SEQ ID NO 8
<211> LENGTH: 31
<212> TYPE: PRT
<213> ORGANISM: Artificial Sequence
<220> FEATURE:
<223> OTHER INFORMATION: signal peptide
<220> FEATURE:
<221> NAME/KEY: PEPTIDE
<222> LOCATION: (1)..(31)

<400> SEQUENCE: 8

Met Lys Tyr Leu Leu Pro Thr Ala Ala Ala Gly Leu Leu Leu Leu Ala
1               5                   10                  15

Ala Gln Pro Ala Met Glu Leu Asp Ile Gly Ile Asn Ser Asp Pro
            20                  25                  30

<210> SEQ ID NO 9
<211> LENGTH: 22
<212> TYPE: PRT
<213> ORGANISM: Artificial Sequence
<220> FEATURE:
<223> OTHER INFORMATION: connected protein
<220> FEATURE:
<221> NAME/KEY: PEPTIDE
<222> LOCATION: (1)..(22)

<400> SEQUENCE: 9

Glu Phe Gly Gly Gly Gly Ser Gly Thr Ala Ser Arg Pro Val Asp Lys
1               5                   10                  15

Leu Ala Ala Ala Leu Glu
            20

<210> SEQ ID NO 10
<211> LENGTH: 75
<212> TYPE: PRT
<213> ORGANISM: Artificial Sequence
<220> FEATURE:
<223> OTHER INFORMATION: E.coli outer membrane protein intimin domain 2
<220> FEATURE:
<221> NAME/KEY: PEPTIDE
<222> LOCATION: (1)..(75)

<400> SEQUENCE: 10

Asn Lys Val Asp Ile Ile Gly Asn Asn Val Arg Gly Glu Leu Pro Asn
1               5                   10                  15

Ile Trp Leu Gln Tyr Gly Gln Phe Lys Leu Lys Ala Ser Gly Gly Asp
            20                  25                  30

Gly Thr Tyr Ser Trp Tyr Ser Glu Asn Thr Ser Ile Ala Thr Val Asp
        35                  40                  45

Ala Ser Gly Lys Val Thr Leu Asn Gly Lys Gly Ser Val Val Ile Lys
    50                  55                  60

Ala Thr Ser Gly Asp Lys Gln Thr Val Ser Tyr
65                  70                  75

<210> SEQ ID NO 11
<211> LENGTH: 370
<212> TYPE: PRT
<213> ORGANISM: Artificial Sequence
<220> FEATURE:
<223> OTHER INFORMATION: Maltose-binding protein
<220> FEATURE:
<221> NAME/KEY: PEPTIDE
<222> LOCATION: (1)..(370)
```

<400> SEQUENCE: 11

```
Lys Ile Glu Glu Gly Lys Leu Val Ile Trp Ile Asn Gly Asp Lys Gly
1               5                   10                  15

Tyr Asn Gly Leu Ala Glu Val Gly Lys Lys Phe Glu Lys Asp Thr Gly
            20                  25                  30

Ile Lys Val Thr Val Glu His Pro Asp Lys Leu Glu Glu Lys Phe Pro
        35                  40                  45

Gln Val Ala Ala Thr Gly Asp Gly Pro Asp Ile Ile Phe Trp Ala His
    50                  55                  60

Asp Arg Phe Gly Gly Tyr Ala Gln Ser Gly Leu Leu Ala Glu Ile Thr
65                  70                  75                  80

Pro Asp Lys Ala Phe Gln Asp Lys Leu Tyr Pro Phe Thr Trp Asp Ala
                85                  90                  95

Val Arg Tyr Asn Gly Lys Leu Ile Ala Tyr Pro Ile Ala Val Glu Ala
            100                 105                 110

Leu Ser Leu Ile Tyr Asn Lys Asp Leu Leu Pro Asn Pro Pro Lys Thr
        115                 120                 125

Trp Glu Glu Ile Pro Ala Leu Asp Lys Glu Leu Lys Ala Lys Gly Lys
    130                 135                 140

Ser Ala Leu Met Phe Asn Leu Gln Glu Pro Tyr Phe Thr Trp Pro Leu
145                 150                 155                 160

Ile Ala Ala Asp Gly Gly Tyr Ala Phe Lys Tyr Glu Asn Gly Lys Tyr
                165                 170                 175

Asp Ile Lys Asp Val Gly Val Asp Asn Ala Gly Ala Lys Ala Gly Leu
            180                 185                 190

Thr Phe Leu Val Asp Leu Ile Lys Asn Lys His Met Asn Ala Asp Thr
        195                 200                 205

Asp Tyr Ser Ile Ala Glu Ala Ala Phe Asn Lys Gly Glu Thr Ala Met
    210                 215                 220

Thr Ile Asn Gly Pro Trp Ala Trp Ser Asn Ile Asp Thr Ser Lys Val
225                 230                 235                 240

Asn Tyr Gly Val Thr Val Leu Pro Thr Phe Lys Gly Gln Pro Ser Lys
                245                 250                 255

Pro Phe Val Gly Val Leu Ser Ala Gly Ile Asn Ala Ala Ser Pro Asn
            260                 265                 270

Lys Glu Leu Ala Lys Glu Phe Leu Glu Asn Tyr Leu Leu Thr Asp Glu
        275                 280                 285

Gly Leu Glu Ala Val Asn Lys Asp Lys Pro Leu Gly Ala Val Ala Leu
    290                 295                 300

Lys Ser Tyr Glu Glu Glu Leu Ala Lys Asp Pro Arg Ile Ala Ala Thr
305                 310                 315                 320

Met Glu Asn Ala Gln Lys Gly Glu Ile Met Pro Asn Ile Pro Gln Met
                325                 330                 335

Ser Ala Phe Trp Tyr Ala Val Arg Thr Ala Val Ile Asn Ala Ala Ser
            340                 345                 350

Gly Arg Gln Thr Val Asp Glu Ala Leu Lys Asp Ala Gln Thr Arg Ile
        355                 360                 365

Thr Lys
    370
```

<210> SEQ ID NO 12
<211> LENGTH: 495
<212> TYPE: PRT
<213> ORGANISM: Artificial Sequence -continued

```
<220> FEATURE:
<223> OTHER INFORMATION: E.coli transcription factor
<220> FEATURE:
<221> NAME/KEY: PEPTIDE
<222> LOCATION: (1)..(495)

<400> SEQUENCE: 12
```

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
370                 375                 380

```
Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
            405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
        450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala
                485                 490                 495

<210> SEQ ID NO 13
<211> LENGTH: 55
<212> TYPE: PRT
<213> ORGANISM: Artificial Sequence
<220> FEATURE:
<223> OTHER INFORMATION: protein G C2 domain
<220> FEATURE:
<221> NAME/KEY: PROPEP
<222> LOCATION: (1)..(55)

<400> SEQUENCE: 13

Thr Tyr Lys Leu Val Ile Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55
```

SECONDARY ANTIBODY DETECTED EPITOPE AND PREPARATION OF SAME

CROSS-REFERENCES TO RELATED APPLICATIONS

The present application claims priority to TW 103115717 (the invention title: SECONDARY ANTIBODY DETECTED EPITOPE AND USE THEREOF) filed May 1, 2014, which is incorporated herein by reference in its entirety.

FIELD OF THE INVENTION

The present invention relates to a secondary antibody detected epitope tag and preparation of the same.

BACKGROUND OF THE INVENTION

Protein markers play a crucial role in proteomics research with the coming of post-genome era. The followings are current applications of protein tags and protein markers in western blot: (1) pre-stain protein markers: the multicolored protein marker allows users to clearly observe the staining results of the immunoassay, but it has low-accuracy since the staining process results in changes in heterogeneity and electricity; (2) dye-free protein markers: the previous report discloses that the green fluorescent protein (GFP) and other fused proteins can be used to construct dye-free protein molecular weight markers, which can emit fluorescence and present ladder-like regular bands (Chang M., Hsu H. Y. and Lee H. J. Dye-free protein molecular weight markers. Electrophoresis, 26: 3062-68, 2005). Although the markers are convenient to use, they cannot be heated since GFP would be denatured and lose its function. Without being heated, however, the markers cannot be denatured thoroughly. Thus, the low-accuracy problem still remains unsolved; (3) biotinylated protein marker: the biotinylated protein markers are dye-free but additional biotin label is required. Moreover, in order to be detected by color reaction, these markers need to be labeled with HRP-conjugated anti-biotin antibody or HRP-conjugated avidin, which causes many inconveniences. In addition, biotin labeling may also alter the electric charge of protein marker and result in inaccuracy; (4) his tag or S-tag: these tags can be auto-developed on film simultaneously when using his-tag, S-tag, or E-tag antibodies to detect these tags by western blot. These tags are not popular for the reason that the color presents simultaneously only when his-tag, S-tag, or E-tag antibodies are used to monitor protein expression. Otherwise, adding HRP-conjugated his-tag, S-tag, or E-tag antibodies is needed to activate the color reaction, which makes the procedure quite troublesome; and (5) protein A fusion calibration proteins and easySee western markers: these protein markers contain protein A or protein G which combines with the IgG antibody to enable these protein markers to be auto-detected by the color reaction in the film when interacting with secondary antibodies. But the structure of the protein A or the protein G may be in hinderance to these protein markers' combination with antibodies and thus decrease the detecting accuracy of the molecular weight as heating.

In conclusion, the applications of protein markers nowadays still have many restrictions and inconveniences, such as low-accuracy, denaturation upon heating, non-extensive use Because of these weaknesses, there is a need to develop a protein marker which can be heated, directly detected by the secondary antibody, and auto-detected by color to improve the accuracy and conveniences of its use in the proteomics research.

SUMMARY OF THE INVENTION

The present invention provides a method of preparing a secondary antibody detected protein tag, comprising: constructing an expressing vector, comprising a nucleotide sequence for encoding the secondary antibody detected protein tag, wherein the secondary antibody detected protein tag comprises at least one epitope selected from at least one primary antibody which is detected by corresponding secondary antibody; expressing the expressing vector in a host cell; and obtaining the secondary antibody detected protein tag which is expressed in the host cell.

The present invention also provides a method of preparing a recombinant protein tag for constructing a protein molecular weight marker ladder, comprising: constructing a plurality of recombinant protein expressing vectors, wherein each vector comprises a plurality of nucleotide sequences encoding recombinant proteins of formula (I) independently:

$$(B)_m\text{-}A\text{-}(C)_n \qquad (I),$$

wherein A is a peptide sequence of at least one epitope selected from at least one primary antibody which is detected by corresponding secondary antibody, B and C are mutually identical or different polypeptides, and each of m and n is 0 or any integer larger than 0; expressing the recombinant protein expressing vectors in host cells independently; and obtaining each of the recombinant proteins which is expressed in the host cells having different molecular weights independently.

The present invention further provides a secondary antibody detected protein tag comprises at least two peptide sequences of epitopes, wherein the at least two peptide sequences of epitopes are selected from primary antibodies of at least two different species which are detected by at least two secondary antibodies.

BRIEF DESCRIPTION OF THE DRAWINGS

FIG. 1 (B) shows that the peptides of linear epitope of the mouse primary antibody (M1-M3) are detected by anti-mouse secondary antibody in the western blot. FIG. 1 (C) shows that the peptides of linear epitope of the rabbit primary antibody (R1-R2) are detected by anti-rabbit secondary antibody in the western blot.

FIG. 2 (B) shows that the peptide of the fused linear epitope (M2R2) is detected by anti-mouse secondary antibody in the western blot. FIG. 2 (C) shows that the fused linear epitope (M2R2) is detected by anti-rabbit secondary antibody in the western blot.

DETAILED DESCRIPTION OF THE INVENTION

Figure 1:
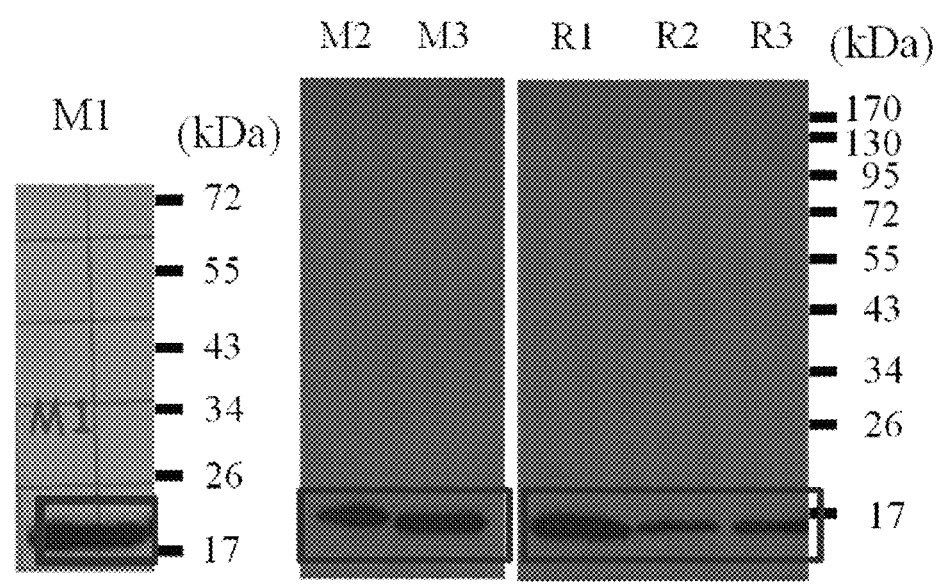
FIG. 1 (A) shows that the peptides of linear epitope of the mouse and rabbit primary antibody (M1-M3 and R1-R3) are recognized by anti-His tag antibody in the western blot.
Figure 1:
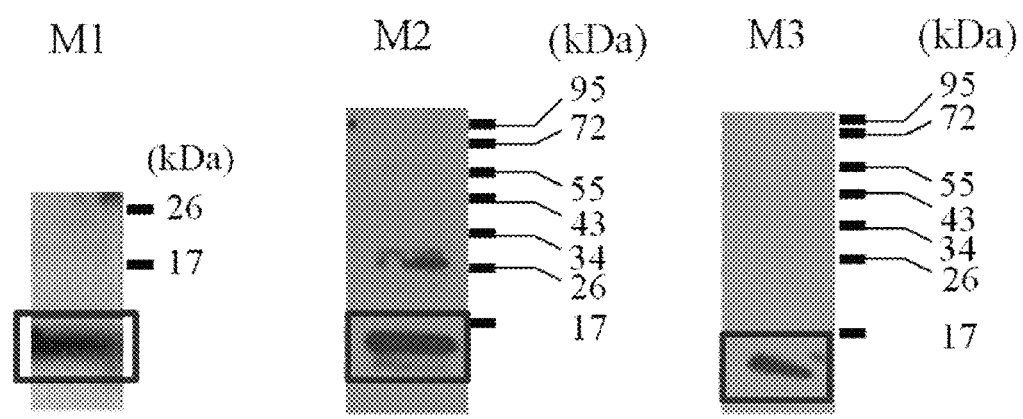
Figure 1:
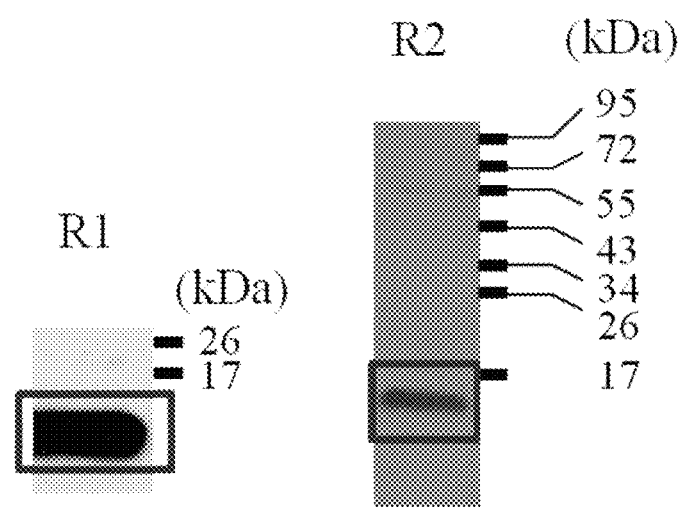

The present invention is more fully appreciated by reference to the following description, including the following glossary of terms and the concluding examples. For the sake of brevity, the disclosures of the publications, including patents, cited in this specification are herein incorporated by reference.

In order to overcome the above disadvantages of the current protein tag, the present invention uses the simulation software of protein structure, such as ABC prep, Bepi prep or C.V.C., to analyze structures of mouse and rabbit primary antibodies, and selects three sequences of linear epitope (LE) from the fragment crystallizable region (Fc region) of mouse IgG antibody (SEQ ID NO: 1, SEQ ID NO: 2 and SEQ ID NO: 3) and three sequences of linear epitope from the Fc region of rabbit IgG antibody (SEQ ID NO: 4, SEQ ID NO: 5 and SEQ ID NO: 6) as candidates based on their crystal structure. The western blot analysis indicates that the SEQ ID NO: 2 and SEQ ID NO: 5 of epitopes have the best recognized ability by anti-mouse and rabbit secondary antibodies, respectively. The present invention further fuses SEQ ID NO: 2 and SEQ ID NO: 5 to form a fusion protein (M&R protein tag), and then assembles with different recombinant proteins to generate a series of recombinant protein markers with 15 to 120 kDa self-revealing molecular weight (M&R linear epitopes recombinant protein marker; M&R LE recombinant protein marker). The M&R LE recombinant protein marker is self-revealed by anti-mouse and rabbit IgG secondary antibodies on film in the western blot.

Therefore, the present invention develops a new protein tag which is obtained from the linear epitopes (LEs) of the Fc region of the mouse and/or rabbit primary antibody which are recognized by the current secondary antibodies (goat anti-mouse secondary antibody and/or goat anti-rabbit secondary antibody). The user can directly use any secondary antibody to make the protein tag containing corresponding epitope be self-revealed by the radio technology or immunoassay and does not need the step of adding primary antibody. In addition, the present invention further constructs the regularly-weighted protein molecular weight marker ladder by fusing the protein tag with epitopes and the recombinant proteins. Through assembling the fusion protein tag comprising the linear epitopes of mouse and rabbit antibody with different recombinant proteins to generate self-revealing regularly-molecular weight markers with a specific range of molecular weight, it provides the user a more accurate positive control in analyzing the protein molecular weight. Thus, the applications of the protein tag of the present invention increase the accuracy, efficacy and conveniences of the detecting method in the proteomics research.

As used herein in the specification, "a" or "an" may mean one or more. As used herein in the claim(s), when used in conjunction with the word "comprising", the words "a" or "an" may mean one or more than one.

The present invention provides a method of preparing a secondary antibody detected protein tag, comprising: constructing an expressing vector, comprising a nucleotide sequence for encoding the secondary antibody detected protein tag, wherein the secondary antibody detected protein tag comprises at least one epitope selected from at least one primary antibody which is detected by corresponding secondary antibody; expressing the expressing vector in a host cell; and obtaining the secondary antibody detected protein tag which is expressed in the host cell.

The term "nucleotide sequence" is intended to mean natural and synthetic linear and sequential arrays of nucleotides and nucleosides, e.g., in cDNA, genomic DNA (gDNA), mRNA, and RNA, oligonucleotides, oligonucleosides and derivatives thereof. It will also be appreciated that such nucleic acids can be incorporated into other nucleic acid chains referred to as "vectors" by recombinant-DNA techniques such as cleavage and ligation procedures.

As referred to herein, the term "encoding" is intended to mean that the gene or nucleic acid may be transcribed in a cell, e.g., when the nucleic acid is linked to appropriate control sequences such as a promoter in a suitable vector (e.g., an expression vector) and the vector is introduced into a cell. Such control sequences are well known to those skilled in the art.

As used herein, the term "expressing vector" refers to composition of matter (e.g., phage, plasmid, viral vectors as well as artificial chromosomes, such as bacterial or yeast artificial chromosomes) used to transmit genetic material into a host cell. A vector may be composed of either DNA or RNA. The vector may be introduced into a host cell by various techniques well known in the art. The regulatory sequence of a vector is a nucleic acid sequence required for expression of a target gene product operably linked thereto. In one embodiment, the expressing vector is a pRSETB plasmid.

By "host cell" is meant a cell that contains an expression vector and supports the replication or expression of the expression vector. Host cells may be prokaryotic cells such as *E. coli*, or eukaryotic cells such as yeast, insect, amphibian, worm or mammalian cells and the like, e.g., cultured cells, explants, and cells in vivo. In one embodiment, the host cell is the BL21 cell.

As used herein, the term "obtaining" includes, but not limited to, the step of extracting.

The term "epitope," as used herein, refers the portion of an antigenic molecule (e.g., a peptide), that is specifically bound by the antibody combining site of an antibody. Epitopes can be formed both from contiguous or juxtaposed noncontiguous residues (e.g., amino acids or nucleotides) of the target molecule (e.g., a protein-protein interface). Epitopes formed from contiguous residues (e.g., amino acids or nucleotides) typically are retained on exposure to denaturing solvents whereas epitopes formed by tertiary folding typically are lost on treatment with denaturing solvents. An epitope typically includes at least 3, and more usually, at least 5 or 8 10 residues (e.g., amino acids or nucleotides). Typically, an epitope also is less than 20 residues (e.g., amino acids or nucleotides) in length, such as less than 15 residues or less than 12 residues. In which, the term "epitope" encompasses both a linear epitope for which the consecutive amino acids are recognized by the antibody as well as a conformational epitope for which the antibodies recognize amino acids to the extent they adopt a proper configuration or conformation. Consequently, in some epitopes, the conformation (three dimensional structure) is as important as the amino acid sequence (primary structure).

As used herein, the term "antibody" refers to a polypeptide comprising a framework region from an immunoglobulin gene or fragment thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Preferable, the terms "light chain variable region" (VL) and "heavy chain variable region" (VH) refer to these light and heavy chains respectively. An antibody includes, but is not limited to, a traditional antibody, a fragment of a traditional antibody containing an antigen binding site, a recombinant antibody containing an antigen binding site, a protein which binds to an antigen, and a product comprising crosslinking any two or more of the above. In which, the fragment of antibody includes, without limitation, Fab, Fab', F(ab')2, and Fv fragments; diabodies; linear antibodies; single-chain antibody molecules; and multispecific antibodies formed from antibody fragments. Also encompassed within the terms "antibodies" are immunoglobulin molecules of a variety of species origins including invertebrates and vertebrates.

"Antigen", as used herein, refers to a substance capable of initiating and mediating an immune response. Antigens that stimulate or potentiate immune responses are said to be immunogenic and may be referred to as immunogens.

The term "fragment crystallizable region (Fc region)" comprises the carboxy-terminal portions of both H chains held together by disulfides. The effector functions of antibodies are determined by sequences in the Fc region, which region is also the part recognized by Fc receptors (FcR) found on certain types of cells.

In one embodiment, the at least one epitope is a liner epitope. Preferably, the at least one epitope is selected from the fragment crystallizable region (Fc region) of the at least one primary antibody. More preferably, the at least one epitope is two epitopes which are selected from primary antibodies of two different species.

In another embodiment, the peptide sequence of the at least one epitope comprises SEQ ID NO: 1, SEQ ID NO: 2, SEQ ID NO: 3, SEQ ID NO: 4, SEQ ID NO: 5, SEQ ID NO: 6 or combination thereof. Among the above peptide sequences, the SEQ ID NO: 1, 2 and 3 are the epitopes of mouse primary antibody, and the SEQ ID NO: 4, 5 and 6 is the epitope of rabbit primary antibody. In a preferred embodiment, the peptide sequence of the at least one epitope is selected from the group consisting of SEQ ID NO: 1, SEQ ID NO: 2, SEQ ID NO: 3, SEQ ID NO: 4, SEQ ID NO: 5 and SEQ ID NO: 6.

In one embodiment, the peptide sequences of the at least one epitope comprise a peptide sequence of first epitope and a peptide sequence of second epitope, wherein the peptide sequence of first epitope is SEQ ID NO: 1, SEQ ID NO: 2 or SEQ ID NO: 3 and the peptide sequence of second epitope is SEQ ID NO: 4, SEQ ID NO: 5 or SEQ ID NO: 6. In a more preferred embodiment, the peptide sequences of the at least one epitope comprise SEQ ID NO: 2 and SEQ ID NO: 5.

The term "primary antibody," as used herein, refers to an antibody that specifically binds to a biological marker of interest present within the biological sample. In certain embodiments the primary antibody may be polymerized. Primary antibodies may be derived from any warm blooded species, e.g. mammals. The primary antibodies can be monoclonal or polyclonal and can be obtained according to standard antibody technology known in the art. The primary antibodies can be from any species, such as rat, horse, goat, rabbit, human, mouse, etc. In a preferred embodiment, the primary antibodies are from rabbit and/or mouse. In another preferred embodiment, the at least two of the primary antibodies in the invention are from different sources or species. In one embodiment, the at least one primary antibody is a mouse primary antibody and/or a rabbit primary antibody.

As used hereinafter, the term "secondary antibodies" refers to antibodies raised against primary antibodies and conjugated to biotin, reporter enzyme or fluorescent agents. Hence, secondary antibodies recognize immunoglobulins of a particular species. The labeled secondary antibodies thus comprises anti-rabbit IgG, anti-mouse IgG, anti-rat IgG, anti-bovine IgG, anti-canine IgG, anti-porcine IgG, anti-caprine IgG, anti-equine IgG, anti-cavia IgG, anti-chicken IgG, anti-feline IgG, anti-camel IgG, or anti-human IgG. The reporter enzyme comprises, for example, alkaline phosphatase or horseradish peroxidase. The fluorescent agent comprises, for example, the Alexa Fluor or Dylight Fluor family. In one embodiment, the corresponding secondary antibody is an ant-mouse secondary antibody and/or an anti-rabbit secondary antibody.

Protein tags are peptide sequences genetically grafted onto a recombinant protein. Often these tags are removable by chemical agents or by enzymatic means, such as proteolysis or intein splicing. Tags are attached to proteins for various purposes. Protein tags find many other usages, such as specific enzymatic modification (such as biotin ligase tags) and chemical modification tag. Often tags are combined to produce multifunctional modifications of the protein. As used hereinafter, the term "protein tag" includes, but not limited to, a protein marker or a protein label.

The present invention also provides a method of preparing a protein tag for constructing a protein molecular weight marker ladder, comprising: constructing a plurality of recombinant protein expressing vectors, wherein each vector comprising a plurality of nucleotide sequences for encoding recombinant protein tags of formula (I) independently:

$$(B)_m\text{-}A\text{-}(C)_n \qquad (I),$$

wherein A is a peptide sequence of at least one epitope selected from at least one primary antibody which is detected by corresponding secondary antibody, B and C are mutually identical or different polypeptides, and each of m and n is 0 or any integer larger than 0; expressing the recombinant protein expressing vectors in host cells independently; and obtaining each of the recombinant protein tags with different protein molecular weight from host cells.

The terms "polypeptide," "peptide" and "protein" are used interchangeably herein to refer to a polymer of amino acid residues. These terms also encompass the term "antibody." In the polypeptide notation used herein, the left-hand direction is the amino (N)-terminal direction and the right-hand direction is the carboxyl (C)-terminal direction, in accordance with standard usage and convention.

In one embodiment, the at least one epitope is a liner epitope. Preferably, the at least one epitope is selected from the fragment crystallizable region (Fc region) of the at least one primary antibody. More preferably, the at least one epitope is two epitopes which are selected from primary antibodies of two different species. The above two epitopes of primary antibody are selected from a mouse primary antibody and a rabbit primary antibody.

In another embodiment, the peptide sequence of the at least one epitope comprises SEQ ID NO: 1, SEQ ID NO: 2, SEQ ID NO: 3, SEQ ID NO: 4, SEQ ID NO: 5, SEQ ID NO: 6 or combination thereof. Among the above peptide sequences, the SEQ ID NO: 1, 2 and 3 is the epitope of mouse primary antibody, and the SEQ ID NO: 4, 5 and 6 is the epitope of rabbit primary antibody. In a preferred embodiment, the peptide sequence of the at least one epitope is selected from the group consisting of SEQ ID NO: 1, SEQ ID NO: 2, SEQ ID NO: 3, SEQ ID NO: 4, SEQ ID NO: 5 and SEQ ID NO: 6.

In one embodiment, the peptide sequences of the at least one epitope comprise a peptide sequence of first epitope and a peptide sequence of second epitope, wherein the peptide sequence of first epitope is SEQ ID NO: 1, SEQ ID NO: 2 or SEQ ID NO: 3 and the peptide sequence of second epitope is SEQ ID NO: 4, SEQ ID NO: 5 or SEQ ID NO: 6. In a more preferred embodiment, the peptide sequences of the at least one epitope comprise SEQ ID NO: 2 and SEQ ID NO: 5.

In another embodiment, the A of formula (I) comprises the polypeptide of SEQ ID NO: 2 and SEQ ID NO: 5. In some embodiments, under the premise without decreasing the developing effect of western blot, the arrangement and construction strategy of protein tags assembling A can be adjusted. Such adjustments include but are not limited to:
(1) in order to achieve the goal of assembling regularly-weighted protein molecular weight marker, such as forming the ladder-like protein molecular weight marker, a tag is allowed to share one or more amino acids to the next tag to adjust the molecular weight;
(2) in order to prevent particular restriction enzyme digestion in the sequences or to meet codon usage bias of cells expressing the recombinant proteins, one or more bases of each tag-encoding DNA can be replaced in favor of construction and expression of recombinant proteins, which assemble the regularly-weighted protein molecular weight markers;
(3) in order to add shorter artificial peptide sequences and adjust the molecular weight of A in formula (I), or to add new restriction enzyme cutting sites, one or more bases of each tag-encoding DNA can be added and/or, eliminated in favor of construction and expression of recombinant proteins, which assemble the regularly-weighted protein molecular weight markers;
(4) in order to enhance the recognition sensitivity of anti-tag antibodies, base(s) of each tag-encoding DNA can be added and/or eliminated to create amino acid(s) helpful to recognition sensitivity of the anti-tag antibodies.

In one embodiment, the B and the C are independent polypeptides with same or different molecular weight. In some embodiments, the B and the C are electric neutral, hydrophilic and/or polypeptides relatively insusceptible to glycosylation to prevent inaccuracy problem of the present recombinant protein as protein molecular weight marker. In a preferred embodiment, the value of molecular weight of formula (I) is a multiple of 5, such as 15, 20, 30 40, 50 60, 70, 100, 120.

In another embodiment, the peptide sequences of the B and the C are selected from the group consisting of SEQ ID NO: 7, SEQ ID NO: 8, SEQ ID NO: 9, SEQ ID NO: 10, SEQ ID NO: 11, SEQ ID NO: 12 and SEQ ID NO: 13. Among these sequences, the arrangement of the peptide sequences in the B or the C comprises one or a plurality of SEQ ID NO: 7, SEQ ID NO: 8, SEQ ID NO: 9, SEQ ID NO: 10, SEQ ID NO: 11, SEQ ID NO: 12 and/or SEQ ID NO: 13, and any possible permutation and combination thereof. In a preferred embodiment, the peptide sequence of the B comprises SEQ ID NO: 8 or SEQ ID NO: 13. In a more preferred embodiment, the peptide sequence of the C comprises SEQ ID NO: 7, SEQ ID NO: 9, SEQ ID NO: 10, SEQ ID NO: 11, SEQ ID NO: 12 and/or combination thereof. Those residual fragments may derive from partial commercially available vector sequences or restriction enzyme recognition sequences, designed for simplifying the recombinant protein construction.

For $(B)_m$-A-$(C)_n$ of the present invention, the flanking region of $(B)_m$, A, and $(C)_n$ may include the residual amino acid sequence resulted from recombinant protein construction. Those residual fragments may derive from partially commercially available vector sequences or restriction enzyme recognition sequences, designed for simplifying the recombinant protein construction.

For the recombinant protein of formula (I), if m=0 and n=0, it is indicated that the recombinant protein consists of polypeptide A; if m=0 and n>0, it is indicated that the N terminal of the recombinant protein tag is polypeptide A; if m>0 and n=0, it is indicated that the C terminal of recombinant protein tag is polypeptide A; if m>0 and n>0, it is indicated that there are other amino acid sequences at the two ends of polypeptide A. In a preferred embodiment, m is 0 and n is 0 or larger than 0, such as various recombinant protein tags shown in FIG. 3. The 15.0 kDa recombinant protein tag is a polypeptide of m=1, n=1, and A is consisting of SEQ ID NO: 2 and SEQ ID NO: 5, B is SEQ ID NO: 8 and C is SEQ ID NO: 7; the 20.0 kDa recombinant protein tag is the polypeptide of m=1, n=1, A is SEQ ID NO: 1, B is SEQ ID NO: 8 and C is consisting of SEQ ID NO: 7 and SEQ ID NO: 9.

The auto-developing and regularly-weighted recombinant protein marker ladder of the present invention further comprises a solvent for stabilizing recombinant proteins. The solvent for stabilizing recombinant proteins extends the shelf-life of the recombinant protein and prevents the protease degradation. The solvent includes but is not limited to Tris-$H_3PO_4$, ethylene diamine tetraacetic acid (EDTA), sodium dodecyl sulfate (SDS), dithiothreitol (DTT), $NaN_3$ and/or glycerol with proper concentration and/or pH value.

In one embodiment, the at least one primary antibody is a mouse primary antibody or a rabbit primary antibody. In another embodiment, the corresponding secondary antibody is an ant-mouse secondary antibody and/or an anti-rabbit secondary antibody.

The term "recombinant protein," as used herein, is a manipulated form of protein, which is generated in various ways to produce large quantities of proteins, modify gene sequences and manufacture useful commercial products. The formation of recombinant protein is carried out in specialized vehicles known as vectors. Recombinant technology is the process involved in the formation of recombinant proteins.

The present invention further provides a secondary antibody detected protein tag, comprising at least two peptide sequences of epitopes selected from primary antibodies of at least two different species which are detected by corresponding secondary antibodies.

In one embodiment, the at least one epitope is a liner epitope. Preferably, the at least one epitope is selected from the fragment crystallizable region (Fc region) of the at least one primary antibody. More preferably, the at least one epitope is two epitopes which are selected from primary antibodies of two different species.

In another embodiment, the peptide sequence of the at least one epitope comprises SEQ ID NO: 1, SEQ ID NO: 2, SEQ ID NO: 3, SEQ ID NO: 4, SEQ ID NO: 5, SEQ ID NO: 6 or combination thereof. In a preferred embodiment, the peptide sequence of the at least one epitope is selected from the group consisting of SEQ ID NO: 1, SEQ ID NO: 2, SEQ ID NO: 3, SEQ ID NO: 4, SEQ ID NO: 5 and SEQ ID NO: 6. In a more preferred embodiment, the peptide sequences of the at least one epitope comprise SEQ ID NO: 2 and SEQ ID NO: 5.

In one embodiment, the primary antibodies of at least two different species are a mouse primary antibody and a rabbit primary antibody. In another embodiment, the corresponding secondary antibodies are the anti-mouse and anti-rabbit secondary antibodies.

The secondary antibody detected protein tag containing the at least epitiope in the present invention is used in analyzing and detecting of protein by the protein immunoblot. The protein immunoblot comprises western blot. The western blot is a electroblotting which is a method in molecular biology/biochemistry/immunogenetics to transfer proteins or nucleic acids onto a membrane by using PVDF or nitrocellulose, after gel electrophoresis.

The linear epitope protein tag of the present invention possesses the following advantage: (1) Convenience: it can automatically develop and expose the film following the addition of proper secondary reagents and offer an additional layer of advantage. (2) Accuracy: The proposed protein markers are dye-free; therefore provide superb accuracy in molecular weights estimate. (3) Heat-resistance: the linear epitopes from Fc region of mouse and rabbit antibody were secondary antibody detectable after boiled. (4) Wide applicable field: antibodies of mouse and/or rabbit origin were the most common use in experiment. (5) As a positive control: it can help the user clearly observe and interpret the molecular weight of the protein. In conclusion, the linear epitope tag obtained from mouse and/or rabbit primary antibody in the present invention not only can be applied for tags of recombinant protein and protein marker, but also can be positive control in proteomic experiment. They maintain great promise for commercialization and excellent marketing outlook, thus offering great competition edge to the participating firms in the future.

EXAMPLES

The examples below are non-limiting and are merely representative of various aspects and features of the present invention.

Example 1

Selection of Linear Epitopes (LEs) of Mouse and Rabbit Primary Antibodies

The present invention used the simulation software of protein structure, such as ABC prep, Bepi prep or C.V.C., to analyze structures of mouse and rabbit primary antibodies. According to the result of the protein structure analysis, the present invention first selected the part or all fragments of Fragment crystallizable region (Fc region) of the immunoglobulin G (IgG) of the above primary antibodies which were detected by corresponding secondary antibodies, such as goat anti-mouse secondary antibody and goat anti-rabbit secondary antibody, and further checked these selected part or all fragments of Fc region whether they were located at the exposure of the protein structure and is a linear epitope (LE). In general, the epitopes of antibody were divided into two categories, conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen. By contrast, linear epitopes interact with the paratope based on their primary structure. A linear epitope is formed by a continuous sequence of amino acids from the antigen.

As shown in table. 1, the present invention selected three peptide sequences of LE from a Fc of a mouse IgG antibody (M1-M3) and three peptide sequences of LE from a Fc of a rabbit IgG antibody (R1-R3) as the candidate peptide sequences of the protein tag to perform following experiments, wherein the M1 is the peptide sequence of SEQ ID NO: 1, M2 is the peptide sequence of SEQ ID NO: 2, M3 is the peptide sequence of SEQ ID NO: 3, R1 is the peptide sequence of SEQ ID NO: 4, R2 is the peptide sequence of SEQ ID NO: 5 and R3 is the peptide sequence of SEQ ID NO: 6.

TABLE 1

The peptide sequence and molecular weight of the LE of mouse (M) and rabbit (R) primary antibodies.

| Code No. | Peptide sequence | SEQ ID NO. | molecular weight (kDa) |
|---|---|---|---|
| M1 | QPIMNT NGSYFVYSKL NVQKSNWEAG NTFTCSVLHE GLHNHHTEKS LSHSPGL | SEQ ID NO: 1 | 5.94 |
| M2 | EFK CRVNSAAFPA PIEKTISKTK GRPKAPQVYTIPPPKEQMAK DKVSLTCMITD | SEQ ID NO: 2 | 5.99 |
| M3 | QPIMNTNGSYFVYSKLNVQKSNWEAGNT FTCSVLHEGLHNHHTEKSLSHSPGL | SEQ ID NO: 3 | 5.94 |
| R1 | PKDT LMISRTPEVT CVVVDVSQDD PEVQFTWYINNEQVRTARPPLREQQFNSTI RVVSTLPIT | SEQ ID NO: 4 | 7.26 |
| R2 | GKEFK CKVHNKALPA PIEKTISKAR GQPLEPKVYTMGPPREELSS RSVSLTCMIN GFYPSDISVE W | SEQ ID NO: 5 | 7.37 |
| R3 | KNGKAEDN YKTTPAVLDS DGSYFLYNKLSVPTSEWQRGDVFTCSVMH EALHNHYTQKS ISRSPGK | SEQ ID NO: 6 | 7.33 |

Example 2

Preparation and Analysis of Linear Epitopes of Mouse and Rabbit Primary Antibodies The present invention first designed and synthesized a coding sequence coding for the M1, M2, M3, R1, R2, and R3 by polymerase chain reaction (PCR) based on Table. 1, respectively, and constructed each of the coding sequences into the pRSETB plasmid. In addition, it made each of the coding sequences contain a His tag after constructing into the pRSETB plasmid. After cloning these pRSETB plasmids, the present invention further transformed each of these 5 pRSETB plasmids into a BL21 *E. coli* and induced the expression of the pRSETB plasmid in the BL21 *E. coli*. The present invention used the western blot to test whether the coding sequence in the pRSETB plasmid was expressed. As shown in FIG. 1(A), the expressing peptides encoded by the coding sequences of the pRSETB plasmids, such as M1, M2, M3, R1, R2, and R3, were detected by the anti-His tag antibody in the western blot. The results showed the peptide sequences of the table. 1 were expressed by the pRSETB plasmid of the BL21 *E. coli*.

Further, the present invention also tested whether these peptides encode by the coding sequences of the pRSETB plasmids of the BL21 *E. coli* were detected by the anti-mouse or anti-rabbit secondary antibodies. Using the western blot, the peptide of linear epitope of linear epitope of the mouse primary antibody (M1-M3) were detected by the anti-mouse secondary antibody as shown in FIG. 1(B). In addition, the peptide of linear epitope of the rabbit primary antibody (R1 and R2) were detected by the anti-rabbit secondary antibody as shown in FIG. 1(C) and R3 also was detected by the anti-rabbit secondary antibody in the western blot (the data not shown). These results demonstrated that the LE peptides of Fc region in the primary antibody selected by the present invention could be directly detected by the secondary antibody.

Example 3

Preparation and Analysis of a Fused Linear Epitope from Mouse and Rabbit Primary Antibodies In order to obtain a fused linear epitope which contained an epitope of mouse primary antibody and an epitope of rabbit primary antibody, the present invention used the restriction enzyme to combine the coding sequence coding for the M2 and the coding sequence coding for the R2 by assembly PCR to obtained a fused coding sequence. The fused coding sequence was constructed into the pRSETB plasmid and further connected a sequence of the His tag after constructing into the pRSETB plasmid. After cloning these pRSETB plasmids, the present invention further transformed the pRSETB plasmids into a BL21 *E. coli* and induced the expression of the pRSETB plasmid in the BL21 *E. coli*.

Figure 2:
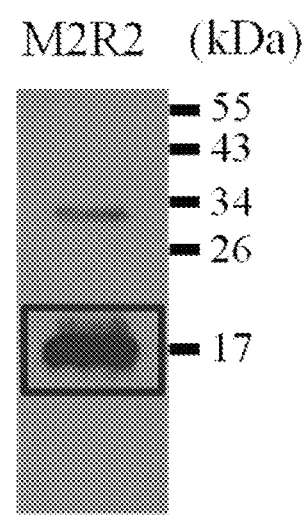
FIG. 2 (A) shows that the peptide of the fused linear epitope (M2R2) is recognized by anti-His tag antibody in the western blot.
Figure 2:
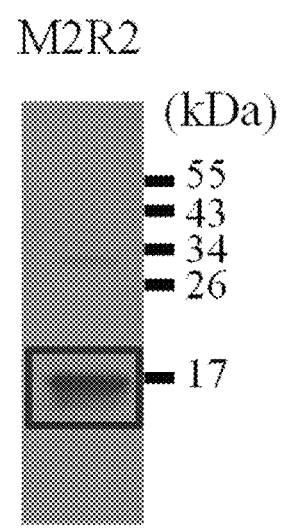
Figure 2:
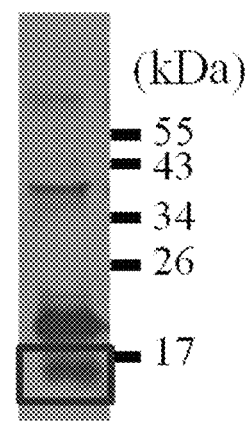

After extracting the fused linear epitope and using the western blot to detect this fused linear epitope, the present invention demonstrated the fused linear epitope (M2R2) encoded by the fused coding sequence of the pRSETB plasmid from the BL21 *E. coli* were in fact detected by the anti-His antibody as shown in FIG. 2(A). The results indicated that the fused peptide sequence of linear epitope (LE) which contained the LE of different species were expressed in the BL21 *E. coli*.

Moreover, the present invention used the anti-mouse secondary antibody and the anti-rabbit secondary antibody to recognize the peptide of fused linear epitope peptide (M2R2) from the mouse and rabbit primary antibodies, respectively. The results demonstrated the M2R2 was directly detected or bounded by the anti-mouse secondary antibody (shown in FIG. 2(B)) and the anti-rabbit secondary antibody (shown in FIG. 2(C)). It implies that a fused protein tag comprising the fused peptide sequence of linear epitope can be directly detected by the secondary antibody.

Example 4

Construction of a Protein Molecular Weight Marker Ladder

Figure 3:
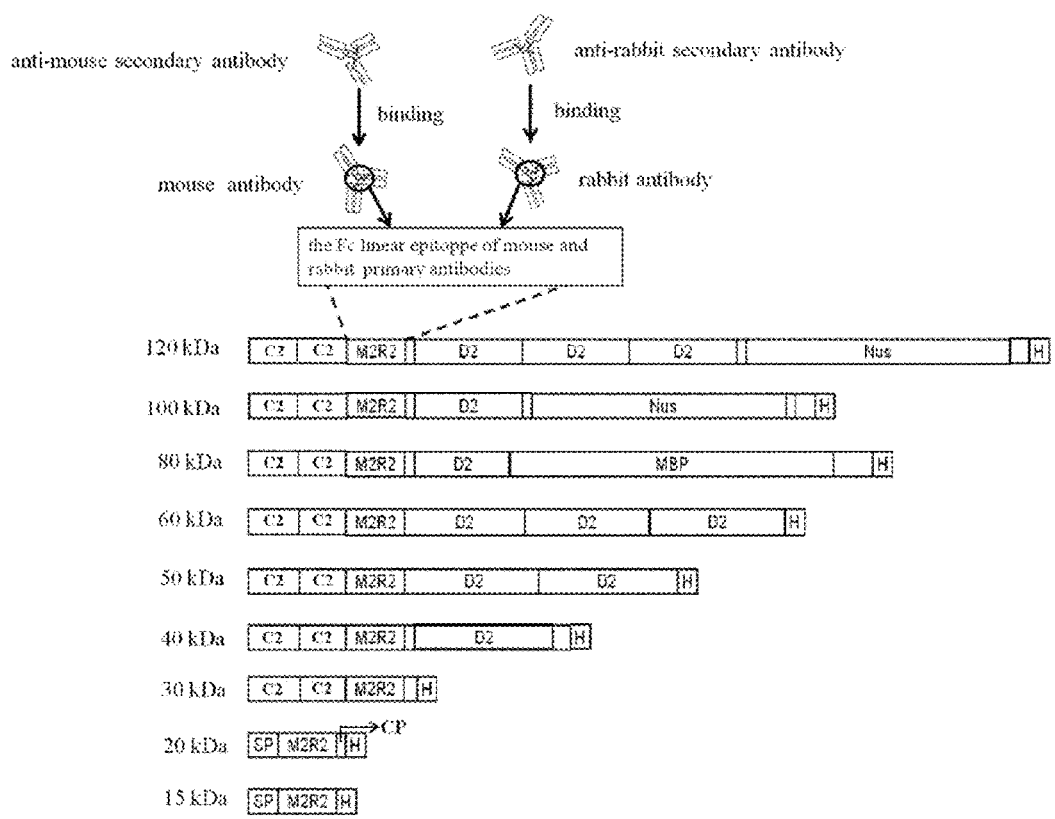
FIG. 3 illustrates the schematic representation of the protein molecular weight marker ladder based on the protein marker containing the fused linear epitope (M2R2) of the present invention, which is auto-developed. The numbers on the left side of the figure represent molecular weight. In order to form the ladder-like protein marker with regular molecular weight, the fused linear epitope is used as a basic recognition unit and connected with H (His tag), SP (signal peptide), CP (connected protein), D2 (O157 E. coli outer membrane protein intimin domain), MBP (maltose-binding protein), Nus (*E. coli* transcription factor) and/or C2 (protein G C2 domain). When detecting target protein with anti-tag antibodies, the protein marker of the present invention is recognized and developed on film at the same time in the western blot.

The following experiment was an application of the protein tag containing the fused linear epitope. The subject of the application in the present invention was to develop a protein molecular weight marker ladder. In order to develop the protein molecular weight markers ladder, the present invention designed and constructed many recombinant protein markers with different protein weight according to a protein weight ordering rule, wherein each recombinant protein marker contained a fused Fc linear epitope and other proteins. First of all, the present invention searched and selected appropriate protein as the composition of the protein marker. As shown in Table. 2, the present invention selected the following proteins: His tag (H, SEQ ID NO: 7), signal peptide (SP, SEQ ID NO: 8), connected protein (CP, SEQ ID NO: 9), O157 *E. coli* outer membrane protein intimin domain (D2, SEQ ID NO: 10), maltose-binding protein (MBP, SEQ ID NO: 11), *E. coli* transcription factor (Nus, SEQ ID NO: 12) and protein G C2 domain (C2, SEQ ID NO: 13). The fused linear epitope containing the epitope of the mouse and rabbit primary antibodies was combined with these proteins with various repetitions to create protein markers of different molecular weights (FIG. 3).

TABLE 2 the peptide sequence and molecular weight of the protein

| Code No. | Peptide sequence | SEQ ID NO. | molecular weight (kDa) |
|---|---|---|---|
| H | HHHHHH | SEQ ID NO: 7 | 0.72 |
| SP | MKYLLPTAAAGLLLLAAQPAMELDIGINSDP | SEQ ID NO: 8 | 3.7 |
| CP | EFGGGGSGTASRPVDKLAAALE | SEQ ID NO: 9 | 2.6 |
| D2 | NKVDIIGNNVRGELPNIWLQYGQFKLKASGGDGT YSWYSENTS IATVDASGKVTLNGKGSVVIKATSGDKQTVSY | SEQ ID NO: 10 | 10 |
| MBP | KIEEGKLVIWINGDKGYNGLAEVGKKFEKDTGIKV TVEHPDKL EEKFPQVAATGDGPDIIFWAHDRFGGYAQSGLLAEI TPDKAFQD KLYPFTWDAVRYNGKLIAYPIAVEALSLIYNKDLLP NPPKTWEE IPALDKELKAKGKSALMFNLQEPYFTWPLIAADGG YAFKYENGK YDIKDVGVDNAGAKAGLTFLVDLIKNKHMNADTD YSIAEAAFNK GETAMTINGPWAWSNIDTSKVNYGVTVLPTFKGQP SKPFVGVLSA GINAASPNKELAKEFLENYLLTDEGLEAVNKDKPL GAVALKSYEEE LAKDPRIAATMENAQKGEIMPNIPQMSAFWYAVRT AVINAASGRQ TVDEALKDAQTRITK | SEQ ID NO: 11 | 40 |

TABLE 2-continued the peptide sequence and
molecular weight of the protein

| Code No. | Peptide sequence | SEQ ID NO. | molecular weight (kDa) |
|---|---|---|---|
| Nus | MNKEILAVVEAVSNEKALPREKIFEALESALATATK KKYEQEIDVR VQIDRKSGDFDTFRRWLVVDEVTQPTKEITLEAAR YEDESLNLGD YVEDQIESVTFDRITTQTAKQVIVQKVREAERAMV VDQFREHEG EIITGVVKKVNRDNISLDLGNNAEAVILREDMLPRE NFRPGDRVR GVLYSVRPEARGAQLFVTRSKPEMLIELFRIEVPEI GEEVIEIKAA ARDPGSRAKIAVKTNDKRIDPVGACVGMRGARVQ AVSTELGGER IDIVLWDDNPAQFVINAMAPADVASIVVDEDKHTM DIAVEAGNLA QAIGRNGQNVRLASQLSGWELNVMTVDDLQAKH QAEAHAAIDT FTKYLDIDEDFATVLVEEGFSTLEELAYVPMKELLE IEGLDEPTVE ALRERAKNALATIAQAQEESLGDNKPADDLLNLEG VDRDLAFKL AARGVCTLEDLAEQGIDDLADIEGLTDEKAGALIM AARNICWFG DEA | SEQ ID NO: 12 | 60 |
| C2 | TYKLVINGKTLKGETTTEAVDAATAEKVFKGYAND NGVDGEWTYDDATKTFTVTE | SEQ ID NO: 13 | 6 |

Example 5

Preparation of a Protein Molecular Weight Marker Ladder

The present invention combined the fused coding sequence coding the M2 and the R2 with other coding sequences coding the H, CP, SP, D2, MBP, Nus or C2 to construct recombinant coding sequences by assembly PCR. These recombinant coding sequences were constructed into the pRSETB plasmids and further connected a sequence of the His tag after constructing into the pRSETB plasmid. After cloning these pRSETB plasmids, the present invention further transformed the pRSETB plasmids into a BL21 *E. coli* and induced the pRSETB plasmids to express recombinant protein markers encoded by the recombinant coding sequences in the BL21 *E. coli* by isopropyl β-D-1-thiogalactopyranoside (IPTG). The BL21 *E. coli* were cultured and pelleted by supercentrifugation, and the pellet was stored frozen after removing the supernatant. The expressing recombinant protein tags were extracted and performed the electrophoresis analysis by SDS-PAGE. After finishing of the electrophoresis, the SDS-PAGE was removed and rinsed in elector-transfer buffer to transfer the recombinant protein markers from SDS-PAGE to nitrocellulose membrane. In the nitrocellulose membrane, the present invention applied western blot using the anti-His antibody to detect the expressing recombinant protein markers.

Figure 4:
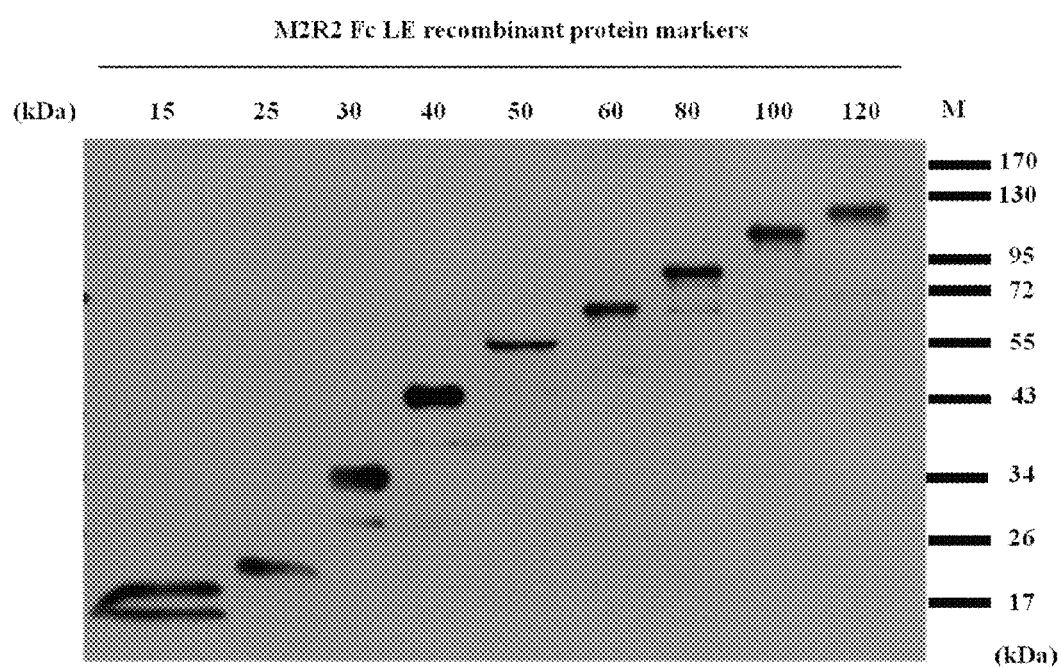
FIG. 4 illustrates the recognition results of recombinant protein markers containing M2, R2 and/or other protein (M2R2 Fc LE recombinant protein markers) with different molecular weights by anti-His secondary antibody in the western blot. The 15 kDa to 120 kDa recombinant protein markers can be developed clearly. M indicates protein marker. The unit of protein molecular weight is kDa.

The present invention created the recombinant protein markers (M2R2 Fc LE recombinant protein markers) containing the M2, R2 and other proteins, wherein the ordering of the molecular weight of the recombinant protein markers was from 15 to 120. As shown in FIG. 4, the western blot was used to prove that the recombinant protein markers (M2R2 Fc LE recombinant protein markers) with different molecular weights were able to be recognized by anti-His antibody and represented as ladder-like bands clearly in the nitrocellulose membrane.

Figure 5:
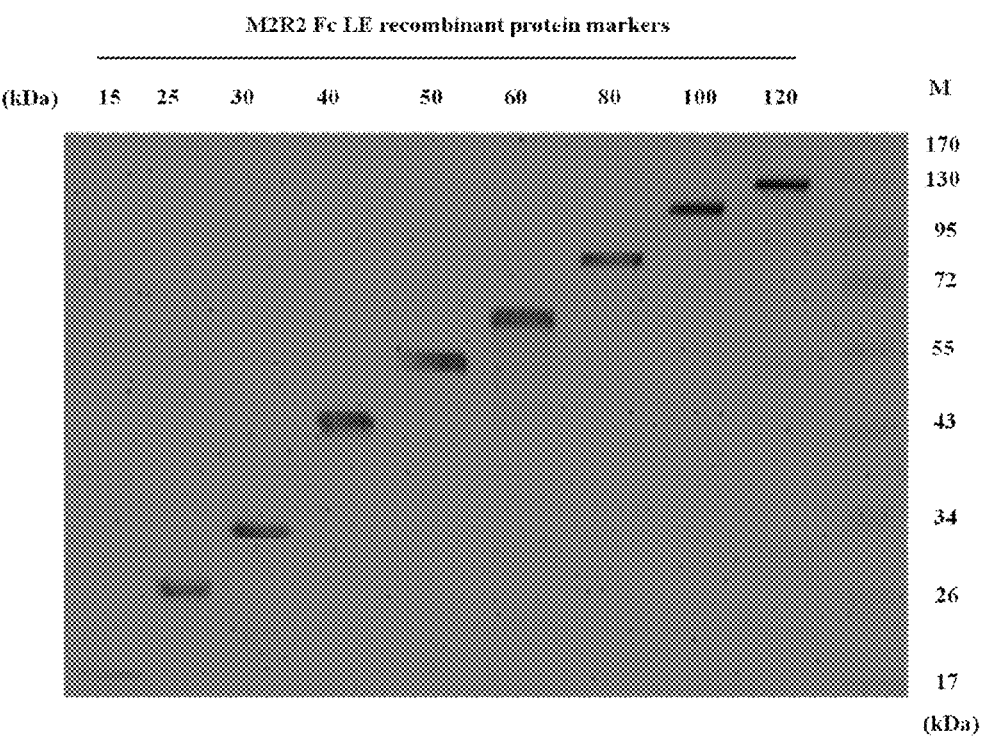
FIG. 5 illustrates the recognition results of recombinant protein markers containing M2, R2 and/or other protein (M2R2 Fc LE recombinant protein markers) with different molecular weights by anti-mouse secondary antibody in the western blot. The 15 kDa to 120 kDa recombinant protein markers can be developed clearly. M indicates protein marker. The unit of protein molecular weight is kDa.

In addition, the present invention further used the anti-mouse secondary antibody to detect the recombinant protein markers (M2R2 Fc LE recombinant protein markers) with ordering molecular weight. As shown in FIG. 5, the western blot was used to prove that the recombinant protein markers with different molecular weights were able to be recognized by anti-His antibody and represented as ladder-like bands clearly in the nitrocellulose membrane. This result demonstrated that the construction of the protein molecular weight marker ladder based on the protein tag containing the fused epitope from the primary antibodies of the different species were directly detected or recognized by corresponding secondary antibody.

Those skilled in the art recognize the foregoing outline as a description of the method for communicating hosted application information. The skilled artisan will recognize that these are illustrative only and that many equivalents are possible.

What is claimed is:

1. A secondary antibody detected protein tag, comprising at least two peptide sequences of epitopes selected from primary antibodies of at least two different species which are detected by corresponding secondary antibodies, wherein the epitopes are selected from the Fc region of the primary antibodies.

2. The secondary antibody detected protein tag of claim 1, wherein the epitopes are liner epitopes.

3. The secondary antibody detected protein tag of claim 1, wherein the primary antibodies of at least two different species are a mouse primary antibody and a rabbit primary antibody.

4. The secondary antibody detected protein tag of claim 1, wherein the at least two peptide sequences of epitopes comprise SEQ ID NO: 2 and SEQ ID NO: 5.

* * * * *